(12) United States Patent
Honkura et al.

(10) Patent No.: US 6,652,278 B2
(45) Date of Patent: Nov. 25, 2003

(54) DENTAL BAR ATTACHMENT FOR IMPLANTS

(75) Inventors: Yoshinobu Honkura, Tokai (JP); Kazuo Arai, Tokai (JP)

(73) Assignee: Aichi Steel Corporation, Tokai (JP)

( * ) Notice: Subject to any disclaimer, the term of this patent is extended or adjusted under 35 U.S.C. 154(b) by 22 days.

(21) Appl. No.: 09/955,073

(22) Filed: Sep. 19, 2001

(65) Prior Publication Data

US 2002/0039719 A1 Apr. 4, 2002

(30) Foreign Application Priority Data

Sep. 29, 2000 (JP) ........................................ 2000-298325

(51) Int. Cl.⁷ ............................................ A61C 13/235
(52) U.S. Cl. ........................................................ 433/189
(58) Field of Search ................................ 433/189, 172, 433/220, 221

(56) References Cited

U.S. PATENT DOCUMENTS

| | | | |
|---|---|---|---|
| 4,184,252 A | * 1/1980 | Krol et al. | .................... 433/172 |
| 4,214,366 A | * 7/1980 | Laban | ......................... 433/189 |
| 4,508,507 A | 4/1985 | Jackson | |
| 4,626,213 A | 12/1986 | Shiner et al. | |
| 4,741,698 A | 5/1988 | Andrews | |
| 4,857,873 A | * 8/1989 | Gillings | ...................... 433/189 |
| 5,678,998 A | 10/1997 | Honkura et al. | |
| 5,931,676 A | * 8/1999 | Honkura et al. | ............. 433/189 |
| 6,203,325 B1 | 3/2001 | Honkura et al. | |

FOREIGN PATENT DOCUMENTS

| | | | |
|---|---|---|---|
| EP | 0 764 428 | 3/1997 | |
| FR | 2 076 270 | 10/1971 | |
| JP | 8-317941 | 12/1996 | |
| WO | 94/20042 | * 9/1994 | .................. 433/189 |

OTHER PUBLICATIONS

Nobel Biocare Product Catalog, "Abutment Connection and Prosthetic Procedure", pp. 3, 22 and 2 cover pages (with Partial English translation).
IMZ Implant System, Monthly report No. 154, 1 page, 1992.
Patent Abstracts of Japan, JP 2001–224604, Aug. 21, 2001.
Patent Abstracts of Japan, JP 08–317941, Dec. 3, 1996 (with corr. EP 0 764 428).

* cited by examiner

*Primary Examiner*—Todd E. Manahan
(74) *Attorney, Agent, or Firm*—Oblon, Spivak, McClelland, Maier & Neustadt, P.C.

(57) ABSTRACT

The present invention is a bar type dental attachment for implants that makes use of magnetic attractive force to secure a denture in place. This bar type dental attachment can rotate corresponding to the movement of the denture during occlusion. The present invention has excellent wear resistance and makes insertion and removal of the denture easy. The present invention has a bar type keeper with an arced attractive face with a constant radius of curvature, and a magnetic assembly that comprises a magnet, a pair of yoke plates sandwiching the magnet, and a seal material made of anticorrosive non-magnetic material that covers the magnet and is hermetically sealed. The attractive surface of the magnetic assembly is curved to fit the keeper.

7 Claims, 2 Drawing Sheets

DENTAL BAR ATTACHMENT FOR IMPLANTS

BACKGROUND OF THE INVENTION

The present invention relates to a bar-type dental attachment that can be used to fix a denture by a magnetic attractive force to the jawbone via dental implants.

PRIOR ART

As shown in FIG. 3 and FIG. 4, in dental treatment there currently exists a bar and clip type dental attachment used to fix a denture to an implant. In this type of attachment, the denture is clipped to a cylindrically shaped bar 41, which is supported by a fixed base embedded in the jawbone, with clips 42 implanted in the denture base. In this attachment, clips fix the denture elastically.

But using this clip and bar type dental attachment, one must press the clips made of mental or plastic on to the bar when putting in the denture and denture is not easily inserted. Furthermore, there is a problem of wear between the clips and the bar.

On the other hand, as is shown in laid-open Japanese patent number 8-317941, there are have been many attempts to use magnetic attractive force to fix a denture to implants because dentures are easily inserted and removed when fixed via magnets.

But these prior attachments using magnetic attractive force are abutment type attachments, which differ from bar type attachment. Furthermore, in these prior attachments, the attractive face between the magnetic assembly embedded in the denture base and the keeper embedded in the abutment is a flat surface. So, the prior attachments using magnetic force cannot revolve according to the movement of the denture during occlusion because said attractive face is a flat surface. And the magnetic assembly embedded in denture base cannot be used with this bar type keeper because the contact face of said bar type keeper has a cylindrically shaped lateral face and the two pieces will not fit.

Considering these problems, the present invention offers a bar type dental attachment for implants, which can revolve according to the movement of the denture during occlusion, is easy to insert and remove, and is highly resistant to wear.

SUMMARY OF THE INVENTION

The present invention of a bar type dental attachment for use with implants comprises a bar shaped keeper which is supported by a fixed base embedded in the jawbone and has at least one section that is an arced attractive surface whose radius of curvature is fixed, and a magnetic assembly comprising: a magnetic body whose magnetic polls face the yoke plates; a pair of yokes which is arranged on both sides of said magnetic body in a sandwich-like fashion, each of which has an attractive face opposite to said attractive face of said keeper, and which fit easily to said attractive face of said keeper; a seal part made of anticorrosive non-magnetic material which hermetically seals at least a part of the lateral face of said magnetic body between said pair of said yoke plates.

The present invention of a bar type dental attachment for implants makes it easy to insert or remove a denture because the denture is fixed to the implants by magnetic attractive force. That is, it is different from prior attachments, which fix dentures elastically by using clips, because it is unnecessary to insert the denture precisely or to press the denture in, and it is possible to insert or remove the denture with a simple motion.

Because the pair of yoke plates of the magnetic assembly of presently invented dental attachment has an attractive face whose shape fits to the arc shaped section of the bar type keeper, the magnetic assembly fits to the keeper well. The present invention also has single-axis rotation and can move corresponding with the seesaw movement of the denture during occlusion. In addition, because the pair of said yoke plates is arranged on both sides of the magnetic body like a sandwich and the magnetic circuit is closed, the magnetic attractive force between the keeper and the magnetic assembly is strong, so the present attachment can sufficiently retain denture.

Because the seal part made of anticorrosive non-magnetic material hermetically seals at least a part of the lateral face of the magnetic body between the pair of yoke plates, and because the entire circumference of the magnetic body is completely enclosed by said yoke plates and seal part, the magnetic body is not corrosive even though a magnet itself is relatively easy to corrode inside the oral cavity.

This seal part, being welded hermetically between a pair of yoke plates, can be a ring-shaped cap that covers the lateral face of the magnetic body. The structure, in which a ring-shaped cap covers the lateral face of a magnetic body and the pair of yoke plates is exposed, enables magnetic body, as is mentioned above, to avoid corrosion while the entire volume of the magnetic assembly is kept small. Therefore, the dental attachment becomes a more suitable size to be used in the mouth.

Furthermore, the magnetic assembly of the present bar type dental attachment for implants can have a convex, or a concave part on the lateral face opposite to said attractive face. With such a concave or convex part, the magnetic assembly can be fixed more firmly to the denture base. Even though the magnetic assembly is embedded in a dental base with adhesive resin, after long use, separation from denture base may occur. By forming said convex or concave part, the magnetic assembly is fixed under a condition wherein said concave part digs into the denture base, or said concave is filled with the denture base. Therefore separation of the magnetic assembly and denture base can be more surely prevented.

The present invention of a bar type dental attachment for implants can have a primer coat on the surface of the magnetic assembly except for the attractive face. The primer coat has a function similar to that of said convex or concave part, in that the magnetic assembly is more firmly fixed with resin material of denture base.

And preset invented bar type dental attachment for implants can have a surface treatment on said attractive face to enhance the resistance to wear. By giving a surface treatment to the attractive surface in contact with a keeper, wear on the attractive face of the magnetic assembly during occlusion or over repeated insertion and removal can be diminished and the dental attachment can have a longer life.

These and other features, advantages and objects of the present invention will be further understood and appreciated by those skilled in the art by reference to the following specification, claims and appended drawings.

THE PREFERED EMBODIMENT OF THE PRESENT INVENTION

The embodiment of present invented bar type dental attachment for implants is explained as follows.

Figure 1:
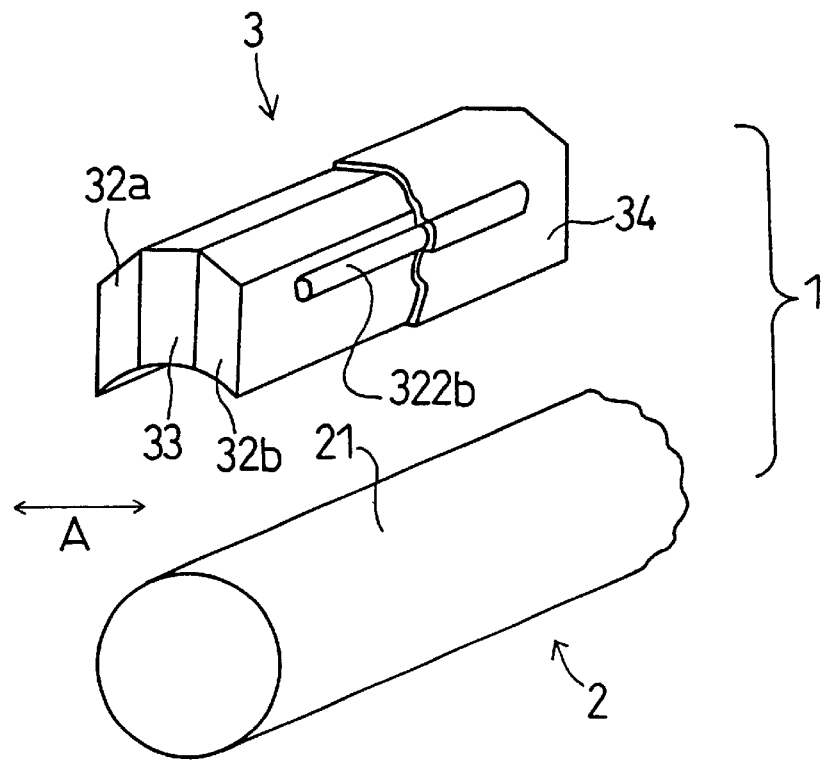
FIG. 1 is a perspective view of the representative embodiment of a bar type dental attachment for implants.
Figure 2:
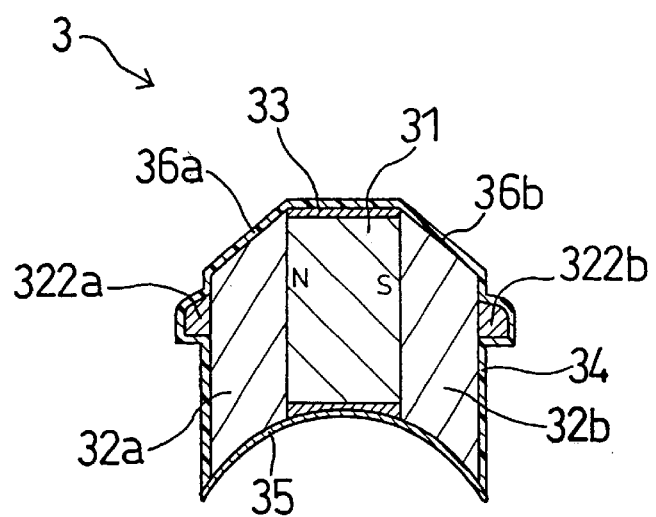
FIG. 2 is a magnified vertical cross section of a part of the representative embodiment of the present invention of a bar type dental attachment for implants.
Figure 3:
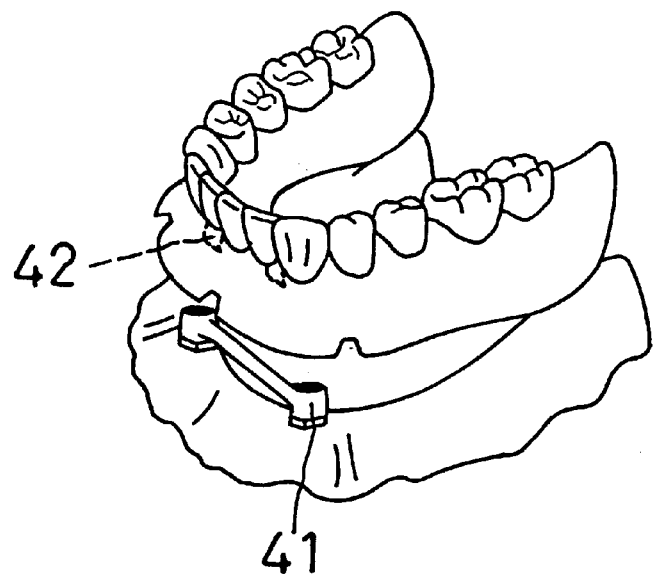
FIG. 3 is an illustration of insertion of prior clip type attachment.
Figure 4:
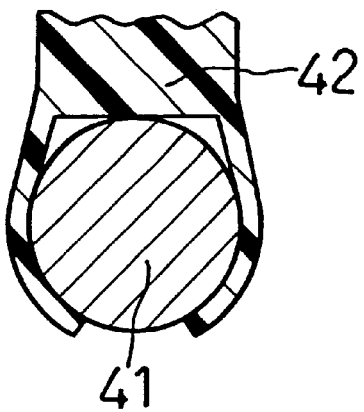
FIG. 4 is a cross section showing the constitution of prior clip type attachment.

A perspective view of the representative embodiment of the present invention of a bar type dental attachment for implants is shown in FIG. 1 and a magnified vertical section of magnetic assembly composing the dental attachment is shown in FIG. 2.

As is shown in FIG. 1, the dental attachment 1 of present embodiment comprises the cylindrically shaped keeper 2 made of magnetic material and the magnetic assembly 3 attracted by magnetic attractive force to the cylindrically shaped lateral attractive face of keeper 2.

First, the keeper 2 is explained. The keeper 2 has a cylindrical shape and is made of 19Cr—2Mo—0.2Ti. The keeper 2 has a cylindrical shape in the present embodiment, but the shape is not limited to this shape, as long as it is a bar shape and it has at least a part of the attractive face whose arced section has a fixed radius of curvature. For example, a bar shaped keeper with a crescent-shaped or ellipse-shaped section with a fixed radius of curvature can be used.

Although 19Cr—2Mo—0.2Ti is used as a material to form the keeper 2 in the present embodiment, many kinds of dental anticorrosive magnetic material that have previously been used to make a keeper for dental attachments which use a magnetic attractive force, can be used as a material to form a keeper. As a keeper is used to fix a denture to implants by forming a magnetic circuit with a magnetic assembly, it is preferable to use a magnetic material whose saturation magnetic flux density is more than 1.3 and whose magnetic permeability is more than 3000; chrome-molybdenum alloy, soft magnetic stainless steel 17Cr—2Mo—0.2Ti and the like have such a feature. Therefore, in present invention of a magnetic attachment, said magnetic materials, chrome-molybdenum alloy and the like, can be used to form the keeper.

Additionally, the keeper 2 can be formed by various methods by which metal products are usually manufactured. For example, a keeper can be made by casting one, or two or more kinds of metals that have been melted and mixed, in a cylinder shaped mold.

Next, the magnetic assembly 3 is explained. The magnetic assembly 3, as is shown in FIG. 1 and FIG. 2, comprises: the plank shaped magnetic body 31 which has the N pole and S pole in the direction of thickness A and is made of Nd—Fe—B— based rare earth magnet; a pair of yoke plates 32a, 32b which is arranged on both lateral faces of the magnetic body 31 in the direction of thickness A and made of 19Cr—2Mo—0.2Ti; and the ring-shaped cap 33 made of stainless steel which is hermetically welded between the pair of yoke plates 32a and 32b, and covers the lateral face of the magnetic body 31 between said yoke plates. The attractive face of the pair of yoke plates 32a and 32b and the ring-shaped cap 33 has a shape which fits said attractive face 21.

Furthermore, the magnetic assembly 33 has belt like convex parts 322a and 322b on both outer lateral faces of the pair of yoke plates 32a and 32b and has inclined faces 36a and 36b descending towards the outer direction on the upper edges of said yoke plates. The surface, except for that opposite to the contact face 21, has a resin coat 34 to make adhesion to the dental base firmer. The face opposite to the contact face 21 has a TiN layer 35, which is a surface treatment to improve a resistance to wear.

Although in the present embodiment a Nd—Fe—B based rare earth magnet is used for magnetic body 31, other types of magnetic materials which have been used as a magnetic body for dental attachment which use magnetic attractive force can be used. It is especially preferable to use high energetic product magnetic materials; in practice it is preferable to use magnetic material that has more than 2388 kj/m$^3$ energetic product. These magnetic materials include Sm—Co based rare earth magnets and so on. By using these rare earth magnets for the magnetic body 31 and making the keeper 2 with said soft magnetic stainless steel etc., more than 5N magnetic attractive force can be achieved.

Although in the present embodiment 19Cr—2Mo—0.2Ti is used for yoke plates 32a and 32b, other types of materials, which have been used as yoke plates for dental attachment that use magnetic attractive force, can be used. To prevent corrosion of magnet, it is preferable to use anticorrosive soft magnetic materials. Such materials are Chrome-molybdenum alloy, 17Cr—2Mo—0.2Ti, pure iron, etc.

Although in the present embodiment stainless steel is used as a seal material to cover the magnetic body, as long as it is a non-magnetic material that has excellent anticorrosion characteristics in the mouth, such as Ti alloy, pure Ti or dental-use Pd—Co—Ni alloy, gold alloy, gold-Pd alloy, etc. can be used.

In the present embodiment, the seal material which covers the magnetic body 31 the shape of a ring-shaped cap 33, and in the present embodiment the pair of yoke plates 32a and 32b and the ring-shaped cap 33 which covers the lateral face of the magnetic body 31 are joined by laser welding at the outer edge of their contact face. By using laser welding, the periphery of this contact face between the yoke plates and the ring-shaped cap can be joined with a very fine, smooth weld.

Other measures of joining, for example, electric beam welding, brazing etc. can be used. In this way, when the magnetic body is covered by yoke plates and a ring-shaped cap and is sealed by welding etc., the magnetic body is not likely to corrode.

In the present embodiment, the magnetic assembly 3 has belt like convex parts 322a and 322b on both outer sides of the pair of yoke plates 32a and 32b. This convex part protrudes into the denture base and can fix the magnetic assembly in the denture base firmly. The convex shape is not limited to said belt like shapes; a variety of other shapes, like many convex dots, are possible. Also the shape without convex part is possible. In the event that the seal material encases the magnetic body and the pair of yoke plates, said convex part may be made on both outer sides of said seal material casing.

Also, instead of said convex parts, concave grooves on both outer lateral faces of the pair of yoke plates 32a and 32b are possible. By having concave parts, magnetic assembly is more firmly fixed in the denture base, as the denture base intrudes into the concave grooves. Furthermore, the shape of the concave part is not limited, but a variety of shapes are possible.

In the present embodiment, the magnetic assembly 3 has a resin coat 34 on the surface except for the face opposing contact face 21, as a primer coat that makes the incorporation into the dental base firmer. The resin coat can enhance adhesion to the denture base, like the function of said convex or concave part, by way of enhancing the joint between the magnetic assembly and resin materials etc. As long as the primer can make the joint with dental base firmer, a variety of primers can be used besides resin. Also, a magnetic assembly without a primer coat is possible.

In present embodiment the contact face of magnetic assembly 3 opposing contact face 21 has a TiN layer 35 as a surface treatment that enhances resistance to wear. By giving a surface treatment to the face that attracts the keeper, wear of the contact face of magnetic assembly by occlusion or repeated insertion and removal can be decreased and the lifespan of the dental attachment can be increased. Further, a variety of surface treatments usually used to enhance a resistance to wear are possible; for example, diamond, N, Cr, ceramic and so on can be used as a surface treatment. Also, a contact face to a keeper without surface treatment is possible. In practice, the resistance to occlusion wear without surface treatment is sufficient because the contact face is made of relatively hard metal materials.

In present embodiment, magnetic assembly 3 has inclined faces 36a and 36b that descend to the outer direction on the upper part of both outer lateral faces of the pair of yoke plates 32a and 32b. This can reduce the height of the yoke plate's shoulder parts, and contribute to a small dental attachment that is easy to insert. Furthermore, the magnetic flux density is low at the yoke plate's shoulder part, so an inclined face causes the magnetic attractive force to weaken very little. The shape of the inclined face is not limited; a line-shaped or arc-shaped inclined face or without an inclined face is possible.

Furthermore, said embodiment is only one example and present invention of a bar type dental attachment for implants can be embodied in various ways that the manufacturers themselves can improve or modify.

The handling during insertion and removal as well as the durability of the present invention of a bar type dental attachment for implants that is explained in said embodiment, was evaluated. The prior art clip type attachment was evaluated in a similar way. The evaluation of the handling during insertion and removal as well as durability of the present invention of a bar type dental attachment and the clip type attachment, are explained as follows.

<Present Invention of a Bar Type Dental Attachment for Implants>
(1) The Dental Attachment in the Embodiment Example The dental attachment comprising a cylindrically shaped keeper made of 19Cr—2Mo—0.2Ti that has a diameter of 3 mm, a length of 50 mm and a magnetic assembly that has a thickness of 1.8 mm, a length of 4.8 mm, a height of 1.8 mm was used. The magnet in the magnetic assembly is made of N—Fe—B rare earth alloy and has a thickness of 0.8 mm and a length of 4.6 mm. The pair of yoke plates is made of 19 Cr—2Mo—0.2T and each has a thickness of 0.9 mm, a length of 4.8 mm, and a maximum height of 1.8 mm. The ring-shaped cap of seal material is made of stainless steel and has a width of 1.0 mm, a length of 4.8 mm, a height of 1.6 mm, and a thickness of 0.1 mm.

Also, a belt like convex part which has a thickness of 0.2 mm, a length of 3.6 mm, and a height of 0.3 mm is placed on both outer lateral faces of the pair of yoke plates of the magnetic assembly. And the face of the magnetic assembly opposite the contact face of the keeper has a surface treatment of TiN. The magnetic attractive force of present dental attachment is 6 N. The dental attachment comprised like this is the embodiment example of a dental attachment.

<Clip Type Attachment>
(1) Comparative Example 1 of Clip Type Attachment

The dental attachment comprises a cylindrically shaped bar made of 18K gold alloy that has a diameter of 2 mm, a length of 5 mm, and a clip made of 18K gold alloy that has a thickness of 2 mm, a length of 5 mm, and a height of 3 mm. Also, the clip has a convex part that has a thickness of 2 mm, a length of 3 mm, and a height of 0.3 mm to prevent detachment. Furthermore, present dental attachment, whose clip covers about 80% of the circumference of the bar, has the magnetic attractive force of 8N. The dental attachment comprised like this is comparative example 1 of a dental attachment.

(2) Comparative Example 2 of Clip Type Attachment

The dental attachment comprises a cylinder shaped bar made of 18K gold alloy that has a diameter of 2 mm and a length of 35 mm, and a clip made of polyoxymethylene that has a thickness of 3 mm and a length of 35 mm. Also the clip has a convex part that has the thickness of 3 mm, a length of 10 mm and a height of 1 mm. Furthermore, present dental attachment, whose clip covers about 90% of the circumference of the bar, has a magnetic attractive force of 10N. The dental attachment comprised like this is comparative example 2 of a dental attachment <Evaluation of the Handling During Insertion and Removal and Durability>

The handling during insertion and removal of said embodiment and comparative examples 1 and 2 is evaluated.

The embodiment example of dental attachment does not require an accurate placement or excess force to insert and can be inserted with only a slight effort. And also it is possible to remove with only a limited effort. On the contrary, comparative example 1 and 2 of dental attachment need an accurate placement and a considerable force to insert because the direction of insertion is limited. Therefore present invented dental attachment is proved to be an attachment that can be inserted more easily than prior clip type attachment.

Durability is evaluated by the frequency of removal and by the frequency of occlusion loading of a dental attachment. In dental attachments that use magnetic attractive force, it is one of the conditions of excellent durability that the deterioration of magnetic attractive force is less than 1% if dental attachment is removed 5 times a day for 3 years, that is, after repeated removals of 5000 times. And another condition of excellent durability is that wear of the contact face with a keeper of the magnetic assembly is less than 1 $\mu$m under occlusion that yields denture rotation of 3 degrees repeatedly 1000 times a day for 3 years, that is, after repeated occlusion of one million times.

Furthermore, as the contact face in the embodiment example of a dental attachment is given a surface treatment of TiN layer that has the thickness of 1 $\mu$m, the contact face has a color other than the base color. Therefore, if wear of the contact face by occlusion is more than 1 $\mu$m, the base color appears and shows that the wear is more than 1 $\mu$m.

The embodiment example of a dental attachment has less than 1% deterioration of magnetic attractive force after repeated removal of 10000 times, and has less than 1 $\mu$m of wear of the contact face with the keeper of the magnetic assembly after 2 million repetitions of occlusion loading. Therefore the dental attachment is proved to be excellent in durability and to have a long life.

On the contrary, comparative example 1 of dental attachment cannot sufficiently fix the denture after 1000 removal times because of the deterioration of the retentive force of the clip. Also, after 300,000 repetitions of occlusion loading, the rubbing part between the clip and bar was worn, a separation between clip and bar occurred and the denture could not be sufficiently fixed. Also, comparative example 2 of dental attachment cannot sufficiently fix the denture after 1500 removals, the retentive force dropped and the denture could not be fixed firmly. Furthermore, as is said above, after 500,000 repetitions of occlusion loading, the rubbing part between clip and bar was worn, a separation between clip and bar occurred and the denture could not be fixed firmly.

From above results, present invention of a denture attachment is proven to be excellent in durability and have a very long life.

The present invention of a bar shape dental attachment for implants can fix a denture firmly and the handling during insertion/removal is easy. Also, present invention of a bar type dental attachment for implants can rotate according to the movement of the denture in occlusion and it is excellent in resistance to wear.

What is claimed is:

1. A bar type dental magnetic attachment for use with dental implants comprising:
    a bar-type keeper supported by a fixed base and configured to be embedded in a tooth root, which has at least one section that is an arced attractive surface having a constant radius of curvature; and
    a magnetic assembly extending in a longitudinal direction of said keeper and comprising a magnetic body, at least two yoke plates arranged on both sides of said magnetic body in a sandwich-like fashion, each of said at least two yoke plates having an attractive face on a same lateral side configured to fit with an attractive surface of the keeper, and a seal part including a corrosion-resistant non-magnetic material and configured to hermetically seal at least a part of the lateral face of said magnetic body between said at least two yoke plates,
    wherein magnetic poles of said magnetic body face said at least two yoke plates.

2. The bar-type dental magnetic attachment as set forth in claim 1, wherein said seal part is a ring-shaped cap configured to be hermetically welded between said at least two yoke plates, and wherein said seal part is configured to seal the lateral face of said magnetic body between said at least two yoke plates.

3. The bar-type dental magnetic attachment as set forth in claim 2, wherein a lateral face of said seal part between said at least two yoke plates is configured to fit with said attractive surface of said keeper.

4. The bar-type dental magnetic attachment as set forth in claim 1, wherein a part of a lateral face of said seal part facing said attractive surface has a convex part or a concave part.

5. The bar-type dental magnetic attachment as set forth in claim 1, wherein a surface, excluding a face opposite to said attractive surface, has a primer coat to enhance a conjugation.

6. The bar-type dental magnetic attachment as set forth in claim 1, wherein a surface opposite to said contact surface is given a surface treatment to enhance resistance to wear.

7. The bar-type dental magnetic attachment as set forth in claim 1, wherein said magnetic body is arranged at the center of the attractive face of said keeper in circumferential direction, and said at least two yoke plates are arranged on both sides of said magnetic body.

* * * * *